United States Patent [19]

Taguchi

[11] Patent Number: 4,531,913
[45] Date of Patent: Jul. 30, 1985

[54] DENTAL SYRINGE

[75] Inventor: Mitsukuni Taguchi, Zushi, Japan

[73] Assignee: Takara Nakajima Co., Ltd., Tokyo, Japan

[21] Appl. No.: 611,099

[22] Filed: May 17, 1984

[30] Foreign Application Priority Data

May 26, 1983 [JP] Japan .................................. 58-78141
May 26, 1983 [JP] Japan .................................. 58-78142

[51] Int. Cl.³ .......................................... A61C 17/02
[52] U.S. Cl. ..................................................... 433/80
[58] Field of Search .............................. 433/80, 84, 85

[56] References Cited

U.S. PATENT DOCUMENTS 4,026,025 4/1977 Hunt ....................................... 433/80
4,108,178 8/1978 Batush .................................... 433/80

Primary Examiner—Robert Peshock
Attorney, Agent, or Firm—Warren B. Kice

[57] ABSTRACT

In a dental syringe, compressed air is caused to flow through a passage tube provided in the body of the syringe while whirling, thus resulting in a whirling air flow which is in turn caused to flow toward a nozzle and, in the course of the flowing movement, is heated due to friction between the air flow and the inner wall of the passage tube.

18 Claims, 12 Drawing Figures

FIG. I

DENTAL SYRINGE

BACKGROUND OF THE INVENTION

1. Field of the Invention

The present invention relates to a dental syringe of the three-way type which is designed so that warm water, warm air or warm water-air mixture jet is selectively available from a nozzle without providing an electric means such as electric heater or the like in the body of the syringe.

2. Description of the Prior Art

In the prior-art three-way syringe of this type, the design is made such that compressed air is heated by means of an electric heater of a nichrome wire provided in a compressed air passage extending through the body of the syringe, a heater switch provided on the syringe body, and a transformer provided outside the syringe for reducing a power source voltage to be applied to the heater from the standpoint of safety, so that warm air blast, which is controlled to a pressure approximately equal to the atmospheric pressure, is jetted out of a nozzle portion mounted at the fore end of the syringe body, by operating a lever for compressed air and depressing the aforementioned switch; and water preheated outside the syringe is introduced into the syringe body through a tube provided therein so as to be jetted out of the nozzle portion. However, such a conventional arrangement is disadvantageous in that since an electric heating system is employed as means for heating compressed air as mentioned above, complex operations are involved in mounting the nichrome wire heater, heater switch and so forth; the wiring inevitably turns out complicated, which tends to cause trouble such as breaking of the heater wire, defective contact of the switch or the like; the syringe is so heavy that difficulty is experienced when it is to be handled by a dentist while being gripped by one of his or her hands; and the presence of the electric lead wires causes inconvenience in the handling of the syringe.

SUMMARY OF THE INVENTION

Accordingly, it is an object of the present invention to provide a novel and improved dental syringe which is free from the aforementioned disadvantages of the prior art.

Another object of the present invention is to provide a dental syringe which employs the principle of vortex tube, instead of providing electric means in the body of the syringe to heat compressed air as in the prior art, wherein compressed air is caused to flow through a passage tube provided in the syringe body while whirling, thus resulting in a whirling air flow which is caused to flow toward a nozzle and, in the course of the flowing movement, is heated due to friction between the air flow and the inner wall of the passage tube.

A further object of the present invention is to provide a dental syringe of the type mentioned just above, which is desinged such that the nozzle portion is prevented from being over heated, thereby precluding the possibility that a burn is produced in the mouth of a patient.

A still further object of the present invention is to provide a dental syringe of the foregoing type, which is designed such that exhaust noise resulting from low-temperature air flow exhausted to the ouside is minimized.

Yet another object of the present invention is to provide a dental syringe of the aforementioned type, which is designed such that the shank portion thereof is prevented from being cooled by low-temperature flowing therethrough, when the shank portion is handled by a dentist while being gripped by one of his or her hands, thereby enabling the dentist to comfortably and smoothly carry out dental operations.

Other objects, features and advantages of the present invention will become apparent from the ensuing description taken in conjunction with the accompanying drawings.

DESCRIPTION OF THE PREFERRED EMBODIMENTS

Figure 1:
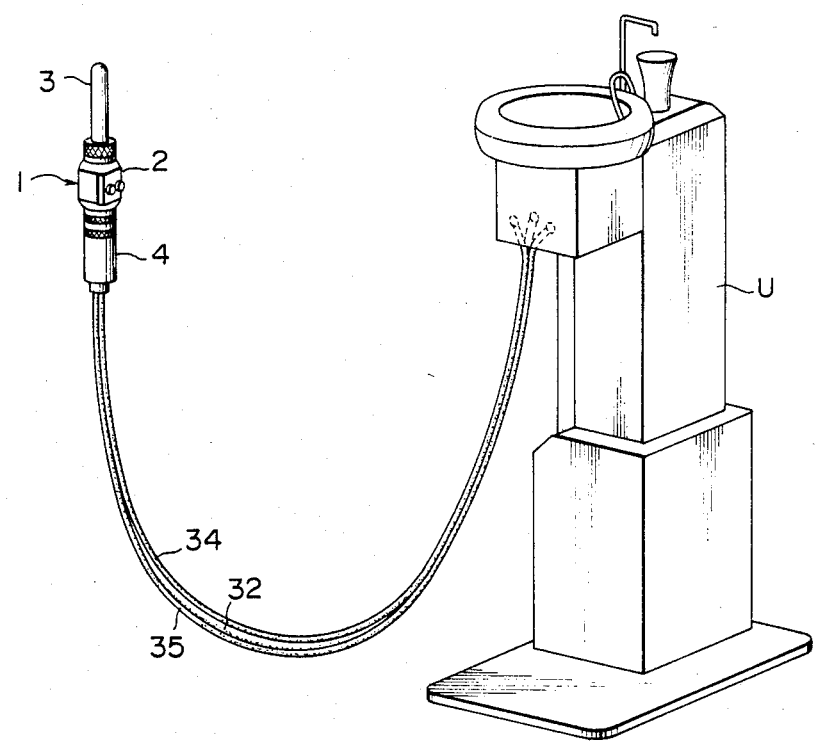
FIG. 1 is a perspective view illustrating the dental syringe according to an embodiment of the present invention as connected to a dental unit.

Referring to FIG. 1, there is illustrated the dental syringe, indicated generally at 1, according to a first emboidment of the present invention, together with a dental unit U to which the dental syringe is connected. The dental syringe 1 comprises a syringe body 2, a substantially rectilinear nozzle portion 3 attached to the fore end of the syringe body 2, and a cylindrical shank portion 4 attached to the rear end of the syringe body 2.

Figure 2:
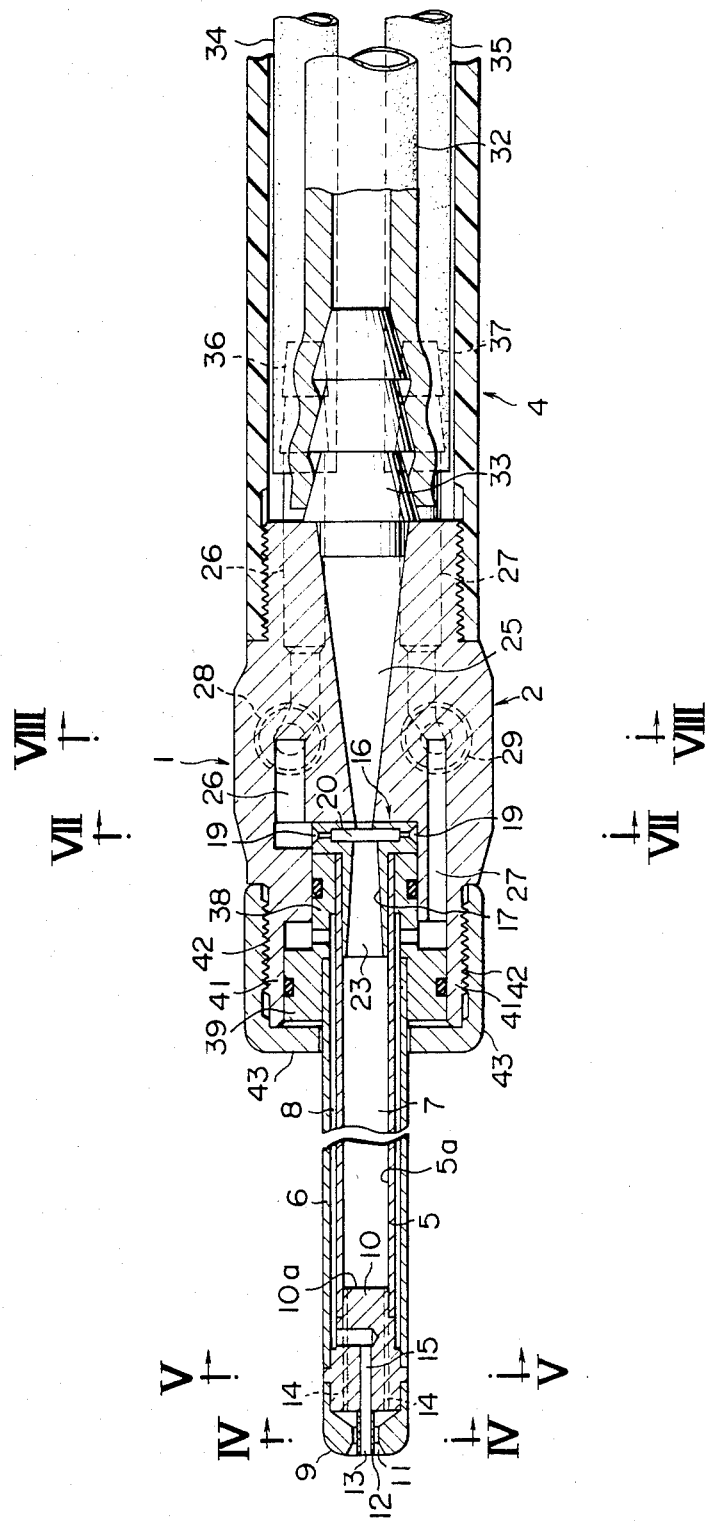
FIG. 2 is a longitudinal sectional view of the dental syringe of the first embodiment shown in FIG. 1.
Figure 3:
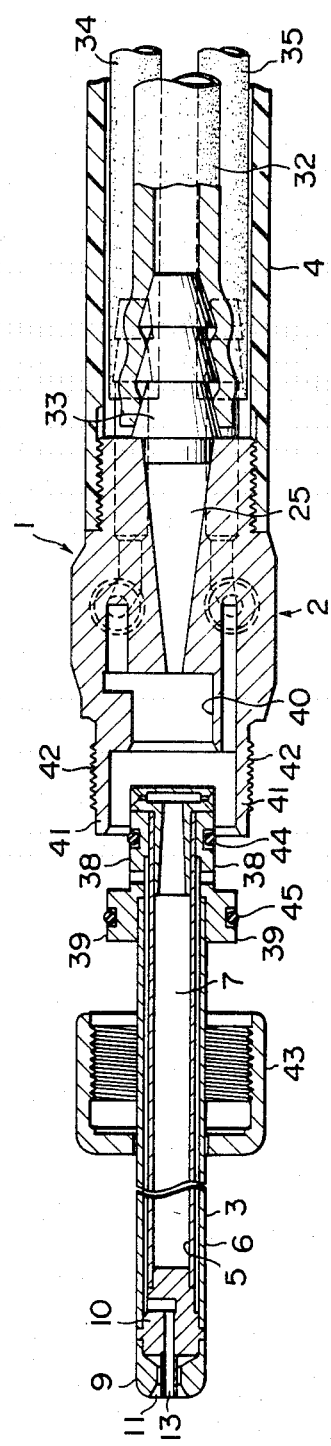
FIG. 3 is a longitudinal sectional view showing a nozzle portion of the dental syringe shown in FIG. 2, with the nozzle portion detached from the body of the syringe.

FIG. 2 is a longitudinal sectional view of the dental syringe 1 shown in FIG. 1. The nozzle portion 3 is detachably mounted onto the syringe body 2 as shown in FIG. 3. The detachable mounting structure will be described in detail hereinafter.

Figure 5:
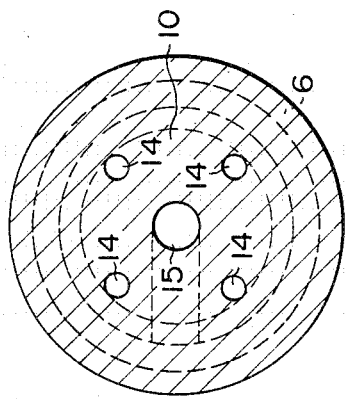
FIG. 5 is an enlarged cross-sectional view taken along lines V—V of FIG. 2.
Figure 4:
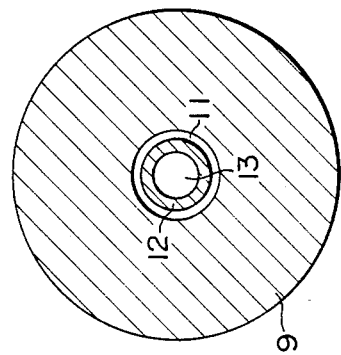
FIG. 4 is an enlarged cross-sectional view taken along lines IV—IV of FIG. 2.
Figure 6:
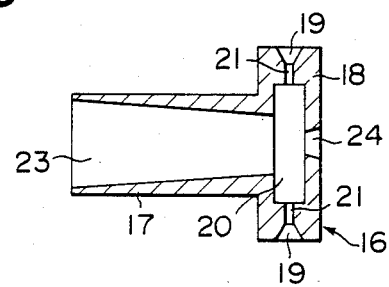
FIG. 6 is a longitudinal sectional view showing a whirling air flow generating member.

As will be seen from FIGS. 2 and 3, the nozzle portion 3 is constructed in the form of a double-tube structure which comprises a whirling air flow transmitting tube attached to the fore end of the syringe body in coaxial relationship therewith, and a sheath tube 6 having a diameter larger than that of the tube 5. The inside space of the whirling air flow trasmitting tube 5 is used as a whirling air flow transmitting passage 7, and the annular space defined between the tubes 5 and 6 is employed as a warm water passage. Attached to the fore end of the nozzle portion 3 are a cap 9 and a flow control member 10 provided behind the cap 9. As shown, in cross-section, in FIG. 4, the cap 9 is formed with an air jet port 11, and the fore end of a small-diameter tube 12 extending from the flow control member 10 is opened at the center of the air jet port 11 so as to define a water jet port 13. As shown, in cross-section, in FIG. 5, the flow control member 10 is formed with four through-holes 14 through which the marginal portion of the whirling air flow transmission passage 7 is communicated with the air jet port 11, and a center through-hole 15 through which the warm water passage 8 between the whirling air flow transmission tube 5 and the sheath tube 6 is communicated with the water jet port 13.

Figure 7:
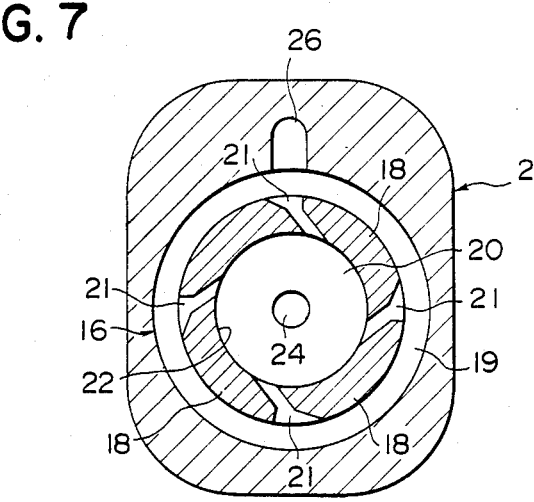
FIG. 7 is an enlarged cross-sectional view taken along lines VII—VII of FIG. 2.

Attached to the rear end of the nozzle portion 3 is a whirling air flow generating member 16 which comprises a hollow cylindrical portion 17 which is adapted to be inserted in the whirling air flow generating tube, and a flange portion 18 of a larger diameter provided at the rear end portion of the cylindrical portion 17 coaxially and integrally therewith. As shown, in cross-section, in FIG. 7, the flange portion 18 is formed with an annular groove 19 extending along the outer periphery thereof, a round disc-like space 20 defined in coaxial relationship with the annular groove 19, and four compressed air nozzles 21 provided in communication with the annular groove 19 and round disc-like space 20. The compressed air nozzles 21 are opened tangentially with respect to the circumferntial wall 22 of the round disc-like space 20. The round disc-like space 20 is communicated, at the front side, with the whirling air flow transmission passage 7 through a space 23 in the cylindrical portion 17, and, at the rear side, with an air exhaust passage 25 formed in the syringe body 2, through a smaller-diameter center hole 24.

Figure 8:
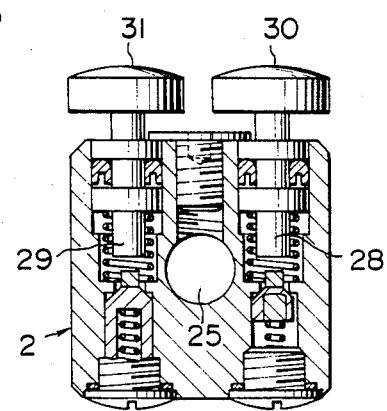
FIG. 8 is an enlarged cross-sectional view taken along lines VIII—VIII of FIG. 2.

The aforementioned air exhaust passage 25 is rearwardly divergent and connected with the small-diameter center hole 24 of the whirling air flow generating member 16, when the nozzle portion 3 is attached to the syringe body 2 with the member 16, so as to constitute a passage contiguous with the center hole 24. Besides the passage 25, the syringe body is also formed with an air feed passage 26 and a water feed passage 27. With the nozzle portion 3 attached to the syringe body 2, the air feed passage 26 is communicated with the annular groove 19 formed in the outer periphery of the whirling air flow generating member 16, and the water feed passage 27 is communicated with the warm water passage 8 defined between the inner whirling air flow transmission tube 5 and the outer sheath tube 6 of the nozzle portion 3. In the passages 26 and 27, there are provided an air feed valve 28 and a water feed vale 29, respectively, such as shown, in cross-section, in FIG. 8. The valves 28 and 29 are actuatable by depressing push buttons 30 and 31 disposed side by side and upwardly projecting out of the syringe body 2, respectively. Mounted at the rear end of the air exhaust passage 25 is an air exhaust tube 32 made of a flexible material, through a connector 33. Also mounted at the rear ends of the air feed passage 26 and water feed passage 27 are an air tube 34 and a water tube 35, which are also formed of a flexible material, through connectors 36 and 37, respectively. The air exhaust tube 32, air tube 34 and water tube 35 extend as far as the dental unit U through the cylindrical shank portion 4 attached to the rear end of the syringe body 2, as shown in FIG. 1.

Figure 9:
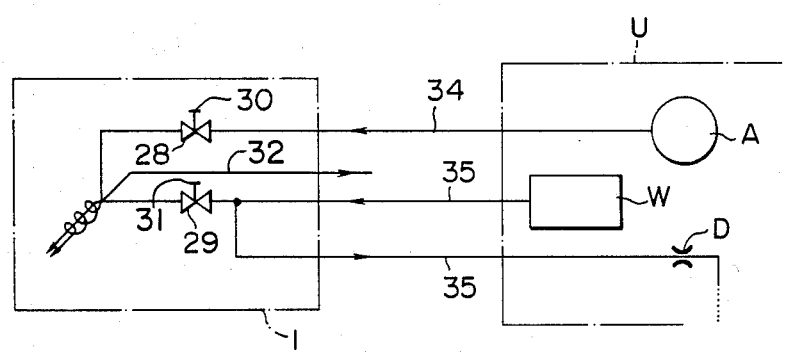
FIG. 9 is a schematic diagram showing the entire system including an air feed passage and a water feed passage.

Referring to FIG. 9, the entire system is shown in a schematic diagram including a compressed air source A and a hot water source W which are provided in the dental unit U. As will be seen from FIG. 9, the air feed tube 34 is coupled to the compressed air source A, while the water feed tube 35 is connected to the warm water source W. In FIG. 9, two such water tubes 35 are provided, one of which serves as a feed tube and the other serves as an exhaust tube, so that warm water may be circulated all the time. A throttle valve D is provided at the end of that one of the water tubes 35 which serves as an exhaust tube. The exahust water tube 35 may be eliminated as in the dental syringe shown in FIG. 2.

As mentioned hereinbefore, the nozzle portion 3 is arranged to be detachably mounted onto the syringe body 2. To this end, as shown in FIG. 3, two annular nozzle supports 38 and 39 are provided on the rear end section of the nozzle portion 3 in coaxially juxtaposed relationship with each other. The rear support 38 is configured for enagagement with a cylindrical recess 40 formed in the syringe body, and the front support 39 is configured for engagement with an annular connecting portion 41 provided on the fore end portion of the syringe body 2. The connecting portion 41 is formed, on the outer surface thereof, with an external thread 42 which serves, together with a tube joint 43, to securely attach the nozzle portion 3 to the syringe body 2. With the nozzle portion 3 secured to the syringe body 2 along with the whirling air flow generating member 16 as shown in FIG. 2, the air passage 26 is diposed in communication with the annular groove 19 of the whirling air flow generating member 16, while the water passage 27 is placed in communication with the warm water passage 8 defined between the whirling air flow transmission tube 5 and the sheath tube 6 of the nozzle portion 3. O rings 44 and 45, which may made of rubber, are fitted in grooves formed in the outer peripheries of the nozzle supports 38 and 39 respectively, thereby securing air-tightness and water-tightness with respect to the air passage 26 and water passage 27 respectively when the nozzle portion 3 is attached to the syringe body 2.

Desription is now be made of the case where it is attempted to clean the interior of the mounth of a patient by means of hot air blast emanating from the above-described dental syringe 1, for example.

The cylindrical shank portion 4 is gripped and the push button 30 provided on the syringe body 2 is depressed by the dentist. Thereupon, the air feed valve 28 is opened so that the air feed passage is established, and thus compressed air available from the compressed air source A is permitted to flow at a high rate into the annular groove 19 of the whirling air flow generating member 16 through the air feed tube 34 and the air passage 26 extending through the syringe body 2. The compressed air flow is in turn jetted, through the four nozzles 21 formed in the flange portion 18, at a super high rate tangentially with respect to the outer periphery of the round disc-like space 20, thus resulting in a whirling air flow along the outer periphery of the round disc-like space 20. Since the center hole 24 formed at the back of the round disc-like space 20 is only small in diameter, the thus resulting whirling air flow is caused to flow forwardly, while whirling along the inner surface of the front cyrindrical portion 17, under the influence of centrifugal force, instead of flowing toward the exhaust passage 25. In this way, the whirling air flow is permitted to pass through the whirling air flow transmission tube 5 and finally reach the fore end of the nozzle portion 3. It is to be particularly noted in this connection that in the course of the transmission of the whirling air flow through the whirling air flow transmission tube 5, friction occurs between the outer portion of the air flow which is whirling at a high speed and the inner wall 5a of the transmission tube 5 and results in heat by which the temperature of the outer peripheral portion of the whirling air flow is elevated, while at the same time the whirling speed thereof is gradually reduced due to the friction between it and the inner wall 5a of the transmission tube 5. The thus heated outer peripheral portion of the whirling air flow is finally permitted to reach the front end of the nozzle portion 3 so as to be jetted, as warm air blast, out of the jet port 11 through the four through-holes 14 formed in the marginal portion of the flow control member 10, and the warm air blast is directed to the desired position in the mouth of the patient.

As mentioned above, the outer peripheral portion of the whirling air flow is heated to a high temperature in the whirling air flow transmission tube 5 due to the heat resulting from the friction with it moves at a high speed in contact with the inner wall 5a of the tube 5. In contrast thereto, however, the inner portion of the whirling air flow is deprived of heat by the outer portion of the whirling air flow and thus maintained at a low temperature. The inner portion of the whirling air flow is then caused to impinge upon the wall face 10a of the flow control member 10 provided at the front end of the nozzle portion 3 so as to be reversed in direction; thus, it is now caused to flow toward the syringe body 2 through the inner portion of tube 5 and then pass through the center portion of the round disc-like space 20 of the whirling air flow member 16 and through the center hole 24 into the exhaust passage 25. Due to the fact that the exhaust passage 25 is divergent as mentioned above, the low-temperature counter flow is decelerated, and then passed, through the exhaust tube 32 connected to the exhaust passage 25, to the dental unit U from which it is exhausted to the external environment.

Although the whirling air flow transmission tube 5 is heated to a high temperature due to the friction between the inner wall 5a thereof and the whirling air flow, it is possible to prevent the nozzle portion 3 from being entirely overheated, by virtue of the fact that the sheath tube 6 is provided outside the tube 5 and the warm water passage 8 is present between the tube 5 and sheath 6. Thus, with the aforementioned arrangement of the present invention, the possibility is precluded that a burn is produced when the nozzle portion 3 is placed in contact with any portion of the mouth of the patient, so that dental operations can be performed safely.

When it is attempted to clean the interior of the mouth of a patient by the use of warm water emanating from the dental syringe 1, for example, the push button 31 provided on the syringe body 2 is depressed so that the water feed valve 29 is opened, and thus warm water available from the warm water source W is passed through the water feed tube 35 and the water feed passage 27 of the syringe body 2, thence through the warm water passage 8 of the nozzle portion 3, and finally jetted out of the jet port 13 provided at the front end of the nozzle portion 3.

By depressing the push buttons 30 and 31 at the same time, both the air feed passage and the water feed passage are established so that an atomized warm mixture of air and water is jetted out of the jet port 13 provided at the front end of the nozzle portion 3.

Although in the foregoing embodiment the flexible exhaust tube 32 was provided at the rear end of the exhaust passage 25, it is possible that the flexible exhaust tube 32 may be eiliminated to cause exhaust to be passed directly to the cylindrical shank portion 4. By providing the exhaust tube 32, however, it is possible to attain such an advantage that exhaust noise can be greatly reduced due to the fact that the whirling air flow is exhausted after having been expanded through the exhaust tube 32. Another advantage is such that by virtue of the fact that whirling air low at a low temperature is exhausted to the outside through the exhaust tube 32, it is possible to prevent the cylindrical shank portion 4 from being cooled to such an extent that the dentist can no longer grip it.

As will be appreciated, the foregoing embodiment is advantageous in that sterilization can readily be effected since the nozzle portion 3 is arranged to be detachably mounted onto the syringe body 2. A further advantage is such that when the nozzle portion 3 is attached to the syringe body 2, connection between the passage 8 and the water feed passage 27 is facilitated by virtue of the dual-tube construction of the nozzle portion 3 wherein the warm water passage 8 is defined between the two tubes 5 and 6.

Figure 10:
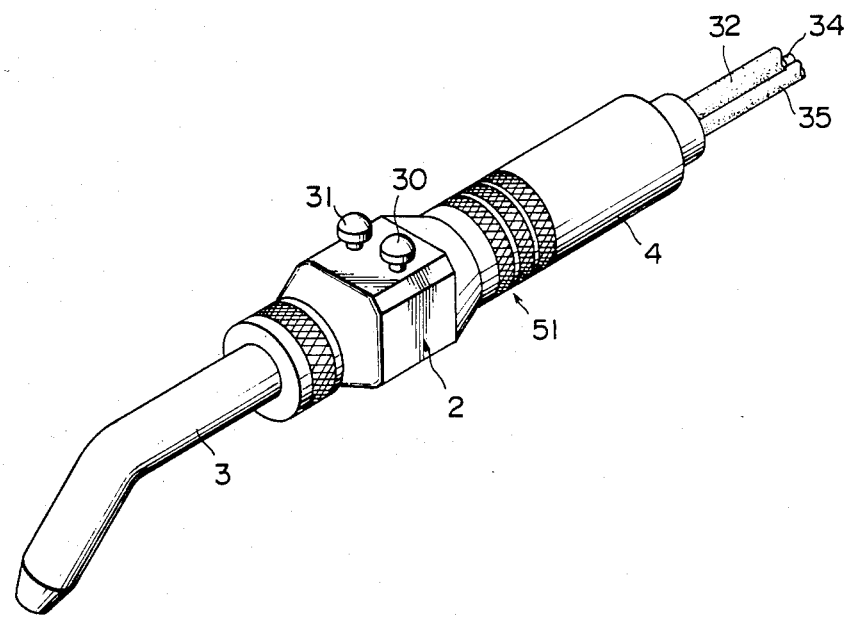
FIG. 10 is a perspective view showing the dental syringe according to a second embodiment of the present invention.
Figure 11:
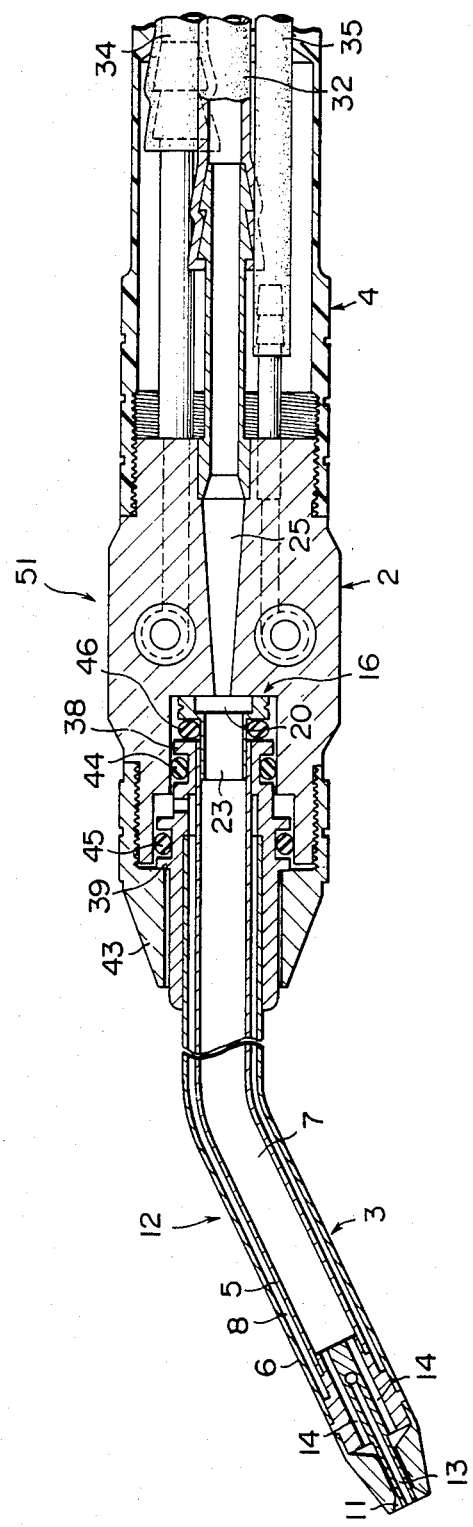
FIG. 11 is a longitudinal sectional view of the embodiment shown in FIG. 10.

Referring to FIGS. 10 and 11 which illustrate the dental syringe according to a second embodiment of the present invention.

The dental syringe, indicated generally at 51, according to this embodiment is similar to the dental syringe 1 according to the first embodiment, except that the nozzle portion thereof is bent at a mid point and the syringe body 2 and nozzle supports 38 and 39 thereof are slightly different in configuration from those of the first embodiment. Therefore, parts of FIGS. 10 and 11 which correspond to those of FIG. 2 are indicated by like reference numerals, and a further explanation thereof will be omitted. According to the second embodiment, an O ring 46 is interposed between the front face of a flange portion 18 of a whirling air flow generating member 16 and the rear face of a nozzle support 38 provided on the nozzle portion 3, and by slightly loosening a tube joint 43, the nozzle portion 3 can be rotated. Thus, by rotating the nozzle portion 3 to a desired position with the tube joint 43 loosened, and then tightening the tube joint, the nozzle portion 3 can be securely attached to the syringe body 2 while assuming the desired position.

Figure 12:
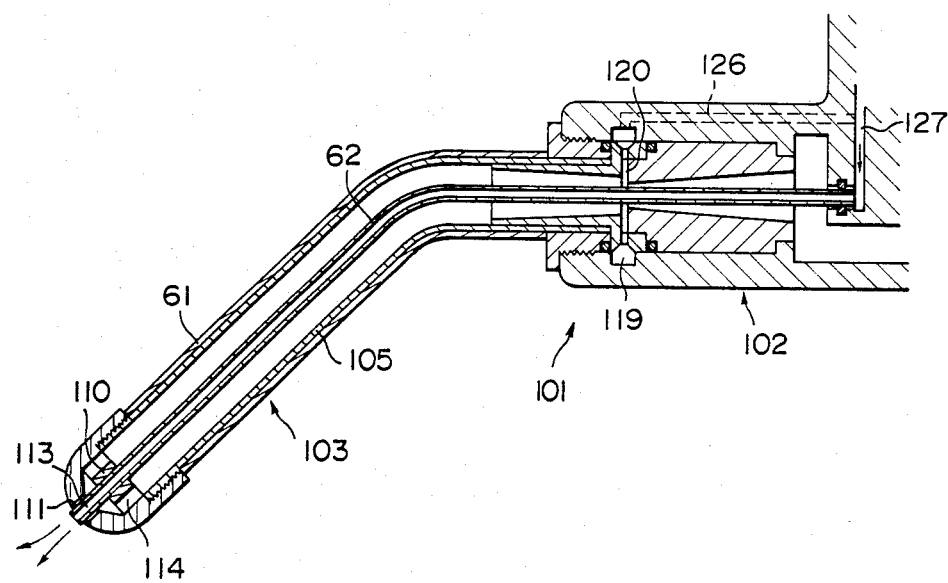
FIG. 12 is a sectional view showing the major portion of the dental syringe according to a third emboidment of the present invention.

FIG. 12 is a longitudinal sectional view showing a nozzle portion 103 of the dental syringe, indicated generally at 101, according to a third embodiment of the present invention. This embodiment is different from the above-mentioned first and second embodiments in that the nozzle portion 103 is not detachable from the syringe body 102 and a whirling air flow transmission tube 105 is covered with a heat insulating material 61. Furthermore, according to this embodiment, the nozzle portion 103 is constructed in the form of a dual-tube structure wherein a heat insulating tube 62 of a small diameter extends from the syringe body 102 through the center portion of a flow control member 110 and is opened, at the front end thereof, to the external environment so as to constitute a jet port 111. The end of the heat insulating tube 62 on the side of the syringe body 102 is disposed in communication with a water feed passage 127 in the syringe body 102.

According to the embodiment shown in FIG. 12, whirling air flow generating means is provided in the syringe body 102, and thus, compressed air which is caused flow in an annular groove 119 of the whirling air flow generating means is jetted into a round disc-like space 120 at a high speed, resulting in a whirling air flow as in the aforementioned first and second embodiments. The resultant whirling air flow is permitted to forwardly move, while whirling, toward the front end of the nozzle portion 103 through a whirling air flow transmission tube 105, and then passed through a plurality of through-holes 114 formed in the marginal portion of the flow control member 110 so as to be jetted out of the jet port 111.

In this embodiment, despite the fact that the heat insulating tube 62 for feeding warm water is coaxially provided in the whirling air flow transmission tube 105, the possibility is precluded that the transmission of the whirling air flow is hindered by the presence of the tube 62, since the whirling air flow in the neighborhood of the center portion of the whirling air flow transmission tube 105 is at a low whirling speed and under a low pressure. Furthermore, even if the center portion of the whirling air flow transmission is cooled by being deprived of heat by the whirling, the possibility is also precluded that warm water passing through the tube 62 is cooled, by virtue of the fact that the tube 62 is formed of a heat insulating material. Still furethermore, since the tube 62, which serves as a water feed passage, is provided in the tube 105, protection for the tube 62 is secured, and the nozzle portion 3 can be constructed to have a reduced diameter.

Another important advantage of the third embodiment is such that even if the tube 105 is heated due to friction between it and the whirling air flow, the possibility is precluded that a burn is produced in the mouth of a patient, since the tube 105 is covered with the heat insulating material 61 as mentioned above.

While the present invention has been illustrated and described with respect to specific embodiments thereof, it is to be understood that the present invention is by no means limited thereto but encompasses all changes and modifications which will become possible within the scope of the appended claims.

I claim:

1. A dental syringe, comprising:
   a syringe body provided therein with an air feed passage coupled to a compressed air source through an air feed tube, and a water feed passage coupled to a warm water source through a water feed tube;
   means for generating a whirling air flow by being supplied with compressed air through said air feed passage;
   a nozzle portion provided therein with a whirling air flow transmission passage for permitting the whirling air flow generated by said whirling air flow generating means to be transmitted therethrough toward the fore end of said syringe, and a warm water passage disposed in communication with said water feed passage, said nozzle portion being attached at the base end portion thereof to the fore end portion of said syringe body through said whirling air flow generating means;
   an air jet port provided at the front end of said nozzle portion for permitting the outer portion of said whirling air flow transmitted through said whirling air flow transmission passage to be jetted to the outside;
   a water jet port provided at the front end of said nozzle portion for permitting warm water introduced from said warm water passage to be jetted to the outside; and
   a cylindrical shank portion mounted at the rear end of said syringe body.

2. A dental syringe according to claim 1, wherein said whirling air flow generating means comprises a flange portion; an annular groove defined in the outer circumference of said flange portion and disposed in communication with the air feed passage of said syringe body; a round disc-like space defined in said flange portion in coaxial relationship with said annular groove; and a plurality of compressed air nozzles providing the communication between said annular groove and said round disc-like space.

3. A dental syringe according to claim 2, wherein said plurality of compressed air nozzles are opened at the inner pehripheral wall of said round disc-like space tangentially with respect thereto.

4. A dental syringe according to claim 2, wherein said round disc-like space is communicated, at the front side as viewed axially, with said whirling air flow transmission passage and disposed in coaxial relationship therewith.

5. A dental syringe according to claim 2, wherein said round disc-like space is communicated, at the rear side as viewed axially, with an exhaust passage formed in said syringe body, through a small-diameter opening provided in coaxial relationship with said round disc-like space.

6. A dental syringe according to claim 5, wherein said exhaust passage is opened in said cylindrical shank portion.

7. A dental syringe according to claim 5, wherein said exhaust passage is connected to an exhaust tube extending through said cylindrical shank portion.

8. A dental syringe according to claim 1, wherein said nozzle portion comprises a small-diameter tube and large-diameter tube which are attached to the front end of said syringe body in coaxial relationship with each other.

9. A dental syringe according to claim 8, wherein said small-diameter tube constitutes said whirling air flow transmission passage, and said warm water passage is defined between said small-diameter and large-diameter tubes.

10. A dental syringe according to claim 8, wherein said small-diameter tube is constituted by a heat insulating tube of a small diameter extending along the axis of said large-diameter tube; said whirling air flow transmission passage is constituted by said heat insulating tube; and said warm water passage is constituted by the remainder of the space in said large-diameter tube.

11. A dental syringe according to claim 10, wherein said large-diameter tube is covered, over the ourter surface thereof, with a heat insulating material.

12. A dental syringe according to claim 1, wherein the outer portion of the whirling air flow transmitted from said whirling air flow generating means toward the front end of said nozzle portion through said whirling air flow transmission passage, is heated due to friction between said outer portion of the whirling air flow and the inner wall of said whirling air flow transmission passage.

13. A dental syringe according to claim 12, wherein said nozzle portion is provided, at the front end thereof, with a flow control member formed with a plurality of through-holes for permitting the heated outer portion of the whirling air flow to be introduced to said air jet port.

14. A dental syringe according to claim 13, wherein said flow control member is provided with a wall face which the cooled inner portion of the whirling air flow transmitted toward the front end of said nozzle portion through said whirling air flow transmission passage is caused impinge upon to as to have the flowing direction thereof reversed, thus resulting in a counter flow directed toward said syringe body.

15. A dental syringe according to claim 14, wherein the cooled inner portion of said whirling air flow converted to said counter flow directed toward said syringe body is caused to flow in said round disc-like space of said whirling air flow generating means, and subsequently pass through said small-diameter hole to be exhausted into the exhaust passage formed in said syringe body.

16. A dental syringe according to claim 1, wherein said nozzle portion is adapted to be detachably mounted onto said syringe body.

17. A dental syringe according to claim 16, wherein said nozzle portion is arranged to be rotatable with respect to said syringe body, and securely attached to said syringe body while assuming a desired position.

18. A dental syringe according to claim 1, further comprising a first and a second valve provided in said syringe body for opening and closing said air feed passage and said water feed passage respectively.

* * * * *